United States Patent
Bateman et al.

[11] Patent Number: 5,879,404
[45] Date of Patent: Mar. 9, 1999

[54] ACETABULAR CUPS AND METHODS OF THEIR MANUFACTURE

[75] Inventors: Ronald James Bateman, Swindon; Robert Andrew Scott, Chippenham, both of United Kingdom

[73] Assignee: Biomet Limited, United Kingdom

[21] Appl. No.: 847,973

[22] Filed: Apr. 21, 1997

[30] Foreign Application Priority Data

Apr. 23, 1996 [EP] European Pat. Off. .............. 96302839

[51] Int. Cl.⁶ ...................................................... A61F 2/32
[52] U.S. Cl. ............................................................ 623/22
[58] Field of Search ........................................ 623/22, 23

[56] References Cited

U.S. PATENT DOCUMENTS

| | | | |
|---|---|---|---|
| 3,723,995 | 4/1973 | Baumann | 623/22 |
| 4,813,960 | 3/1989 | Muller | 623/22 |
| 4,969,910 | 11/1990 | Frey | 623/22 |
| 5,021,062 | 6/1991 | Adrey | 623/22 |
| 5,549,693 | 8/1996 | Roux | 623/22 |
| 5,549,700 | 8/1996 | Graham | 623/22 |
| 5,639,280 | 6/1997 | Warner | 623/22 |
| 5,645,594 | 7/1997 | Devanathan | 623/22 |
| 5,658,345 | 8/1997 | Willi | 623/22 |
| 5,702,478 | 12/1997 | Tornier | 623/22 |

FOREIGN PATENT DOCUMENTS

| | | |
|---|---|---|
| 297789 | 1/1989 | European Pat. Off. . |
| 351545 | 1/1990 | European Pat. Off. . |
| 360734 | 3/1990 | European Pat. Off. . |
| 495341 | 7/1992 | European Pat. Off. . |
| 630624 | 12/1994 | European Pat. Off. . |
| 655230 | 5/1995 | European Pat. Off. . |
| 681845 | 11/1995 | European Pat. Off. . |
| 698382 | 2/1996 | European Pat. Off. . |
| 2 239 980 | 3/1975 | France . |
| 3535959 | 4/1987 | Germany . |
| 4337936 | 5/1995 | Germany . |

*Primary Examiner*—Michael J. Milano
*Attorney, Agent, or Firm*—Harness, Dickey & Pierce, P.L.C.

[57] ABSTRACT

There is described an acetabular cup having an outer shell and an inner liner, which inner liner provides a bearing surface of metallic or ceramic material, wherein there is provided in a position around the rim of the inner liner a shoulder formed of a material that is softer than that used for the head or neck of a femoral component with which the acetabular cup is to be used, which shoulder limits the motion of the femoral component during use. The shoulder may be of a polymeric material such as polyethylene. There is also described an acetabular cup having an inner liner of metallic of ceramic material and an outer shell which is manufactured from a bone cement material. There is further described a method of manufacturing the described acetabular cups which method comprises directly molding the polymeric shoulder of outer shell around the ceramic or metallic inner liner.

12 Claims, 1 Drawing Sheet

ACETABULAR CUPS AND METHODS OF THEIR MANUFACTURE

BACKGROUND OF THE INVENTION

1. Field of the Invention

The invention relates to components to be used in hip prostheses and, in particular, to acetabular cups and components therefor for use in hip prostheses and methods of making such components.

2. Discussion of the Related Art

In replacement hip surgery a femoral component is inserted into the prepared femur. The femoral component has a stem portion which projects into the femoral canal of the prepared femur and has an integral or separate modular head of substantially spherical shape. The ball-like head of the femoral component is received within an acetabular cup component which is implanted in the patient's hip socket, i.e, the acetabulum. The acetabular cup has a substantially hemi-spherical bearing surface for movement of the ball head of the femoral component during action of the joint. The acetabular cup is implanted into the prepared hip socket either with or without cement. Cementless types of acetabular cup may be secured in the prepared bone by a press fit or can be directly screwed in place or otherwise secured in place, for example by indirect means, e.g. by the use of separate bone screws passing through apertures provided in the acetabular cup. Generally, the femoral stem is of metal and the ball head is of metal or of a ceramic material.

Various designs of acetabular cups are available and it is often a multi-piece component having at least a separate outer shell and an inner liner. Where the acetabular cup has an inner liner, that inner liner is generally press-fitted into the outer shell. In some designs of hip prostheses the material of the bearing surface of the acetabular cup, e.g. its inner liner where present, is of the same material as that of the ball head, e.g. for a ceramic head a ceramic bearing surface is provided (a so-called ceramic-on-ceramic prothesis) and for a metal head a metal bearing surface is provided (a so-called metal-on-metal prothesis). In some other designs, the acetabular bearing surface is of polyethylene as the acetabular cup is either provided with a polyethylene inner liner or the acetabular cup is a single component made entirely from polyethylene. The shape of the bearing surface into which the ball head is received affects the degree of movement available after implantation of the joint.

It has been found that the use of polyethylene acetabular bearing surfaces in combination with metal or ceramic femoral ball heads leads to high wear rates of the polyethylene. Aseptic loosening of the separate components due to wear of the polyethylene is now emerging as a major factor in hip prosthesis longevity. As a result, there has been a resurgence of interest in alternatives to the use of polyethylene acetabular bearing surfaces. The wear rate is substantially reduced for metal-on-metal prosthesis and ceramic-on-ceramic prosthesis have been shown in most cases to give an extremely low wear rate and generate very little wear debris. There is, however, in a significant minority of cases the possibility of wear debris, e.g. ceramic or metal particles, becoming trapped between the articulating surfaces which can create further debris by third body wear. This sets up an accelerating spiral resulting in massive wear and loosening of the implant. One of the ways in which this can be initiated is impingement of the head or neck of the femoral component on the rim of the acetabular cup. This is particularly a problem with ceramic ball heads articulating with a ceramic acetabular cup. This can generate ceramic debris which gets between the articulating surfaces.

There is, therefore, a need for an improvement in acetabular cup design so as to provide a prosthesis having low wear characteristics.

SUMMARY OF THE INVENTION

According to a first aspect of the present invention there is provided an acetabular cup having an outer shell and an inner liner, which inner liner provides a bearing surface of metallic or ceramic material, wherein there is provided in a position around the rim of the inner liner a shoulder formed of a material that is softer than that used for the head or neck of a femoral component with which the acetabular cup is to be used, which shoulder limits the motion of the femoral component during use.

The material from which the shoulder is manufactured should be softer than the biomedically acceptable metallic and ceramic materials which are used in the manufacture of prosthetic components and in particular those used in the head or neck of femoral hip prostheses. The material from which the shoulder is manufactured is preferably a biomedically acceptable polymeric material i.e. a biologically compatible material.

With the present invention, the head and neck of the femoral component used is cushioned from damage upon impact with the acetabular cup. With conventional designs of ceramic or ceramic lined acetabular cups, impingement will result in contact between the ceramic rim of the acetabular cup and the metal femoral neck or ceramic ball-head. The very high contact stresses generated can damage the cup rim and can lead to catastrophic wear. With the present invention, the inner liner is provided with a shoulder of softer material, e.g. a biomedically acceptable polymeric material, in which it is in effect recessed so that any impingement will be on that shoulder at the mouth of the cup rather than on the ceramic inner liner. Although there could result with the present invention a generation of a small quantity of debris from the shoulder, that debris will be soft and not cause third body damage to the articulating bearing surfaces.

The shoulder or chamfer may be adjunct to, i.e. an additional part of, the inner line or it may be formed as a component separate therefrom. The shoulder or chamfer is preferably an adjunct to, i.e. a part of, the outer acetabular shell.

Preferably the shoulder extends right around the rim of the inner liner. It should be upstanding from that rim. The femoral head or stem abuts the shoulder or chamfer when it is at one of its limits of motion.

Preferably the whole of the acetabular cup, i.e. the inner bearing surface and the outer shell, is formed of the softer material from which the shoulder is manufactured, e.g. the whole of the acetabular cup is preferably formed from a biomedically acceptable polymeric material.

The shape of the shoulder is of less relevance than the material from which it is formed. It may take the form of a rounded edge or a flat slanting or tapering surface.

Suitable polymeric materials for use in the present invention must be biocompatible and have suitable wear properties, i.e. be wear and abrasion resistant. They are softer than the material of which is made the head or neck of the femoral component with which the acetabular cup is to be used. Suitable biomedically acceptable polymeric materials include polyether ether ketone (PEEK), polymethylmethacrylate (PMMA) or polyethylene (PE). Polyethylene is considered particularly suitable and a high density form such as ultra-high molecular weight polyethylene (UHMWPE) is preferred.

The material of the inner liner, which is to act as a hard wearing bearing surface, is of a metallic or ceramic material. Low friction, abrasion and corrosive resistant metallic and ceramic materials are preferred. Suitable metallic materials include high grade stainless steel, titanium, titanium alloys, zirconium, zirconium alloys, and cobalt chromium alloys such as cobalt chromium molybdenum alloy. The metal may be surface treated or coated, e.g. coated by titanium nitride or diamond-like carbon or by a ceramic coating such as calcium phosphate ceramic coating. Suitable ceramic materials include those such as alumina (aluminum oxide).

The acetabular outer shell of the present invention may be either of the cemented or cementless type. It may be provided with means of furthering the anchoring or engagement of the shell in the bone, e.g. projecting fins or ribs may be provided and if it is of the cementless type it may also be provided with external screw threads for direct screwing into the bone or with holes in which bone screws can be received for indirect screwing. The outer surface of the acetabular shell may be provided with means for encouraging bone ingrowth, e.g. it may have a porous outer coating or be coated with hydroxyapatite.

Problems may arise with conventional cemented acetabular cups in that the interface between the acetabular shell and the cement can be loosened, generally due to mismatching of the materials between the outer shell and the cement. Hence in the case of metal-on-metal prosthetic hips having an acetabular cup having an inner metal bearing liner and an outer polyethylene shell, problems arise when the polyethylene shell is cemented into the acetabulum in a conventional manner. Due to mismatching of the modulus of the polyethylene material and that of the bone cement, bonding between the acetabular shell and the cement is not good and the polyethylene/cement interface can loosen.

There is therefore a need to overcome the problems of conventional acetabular cups having a polyethylene shell and being of cemented form.

According to a second aspect of the present invention there is provided an acetabular cup having an inner liner of metallic or ceramic material and an outer shell which is manufactured from a bone cement material.

With the second aspect of the present invention the outer acetabular shell is formed from a bone cement material which is similar to or may be the same as the cement material which is to be used to anchor the shell in the bones so that the cement bonds well with the outer acetabular shell forming a single mass of material. There is, therefore, no mismatch in modulus between the acetabular shell and the cement, and the interface is strongly, chemically bonded. This eliminates the polyethylene/cement interface of conventional acetabular cups which can be loosened. It is also advantageous to allow the minimum number of components to be used for the acetabular cup. Only the inner liner and an outer shell is required—it not being required to provide additional coatings or mantles—and treatment of the outer shell is not required to promote anchoring in the bone cement.

Materials which are suitable for the manufacture of the outer shell of the acetabular cup include all those known materials which are suitable for use as bone cement such as any suitable acrylic material. The material is preferably a methylmethacrylate polymer or copolymer or a material comprising a methylmethacrylate component.

Where an acetabular cup according to a second aspect of the present invention is also provided with a shoulder or chamfer according to the first aspect of the present invention it is preferred that the material from which the shell is formed is the same as that of which the shoulder is formed so that the advantages of both the first and second aspects of the present invention are achieved.

The acetabular cups according to the first and second aspects of the present invention can be manufactured using any suitable methods, e.g. the acetabular shells can be formed separately from the liners. The shells can, for example, be made by conventional molding techniques and if necessary machined into shape after molding. Alternatively the acetabular shells can be formed from more than one component, which components are press fitted or locked together to form a single outer acetabular shell, It is preferred, however, that the acetabular shell is a single component. The ceramic or metallic inner liners may be press-fitted into the finished acetabular shells.

With conventional acetabular cups where the inner liner is simply press-fitted into the outer acetabular shell, the separate components can become loosened from each other and this can allow debris to come between the component parts.

There is, therefore, a need for improvements in the manufacture of acetabular shells.

According to a third aspect of the present invention there is provided a method of manufacturing an acetabular cup having a metallic or ceramic liner and an outer shell, wherein a shoulder around the liner or the outer shell of the acetabular cup is formed of a biomedically acceptable polymer, which method comprises directly molding the polymeric shoulder or outer shell around the inner liner.

An acetabular cup manufactured according to the third aspect of the present invention provides a good and much more secure fitting between the inner liner and outer shell.

Any suitable molding technique, such as injection or more preferably compression molding, may be used. The polymeric material is preferably molded from its ) powder form and the heat and other conditions required would be well known to one skilled in the art. Some polymeric materials, e.g. PMMA, can also be cast in such a molding process if also encompassed within the third aspect of the present invention.

The outer acetabular shell can be molded around the inner liner directly into its desired shape or it can be molded onto the inner liner as a block and thereafter machined into the required shape after the molding has taken place.

Suitable materials for the biomedically acceptable polymer are as given for the first and second aspects of the present invention specified above.

The method of the third aspect of the present invention may be used to make acetabular cups according to either the first and/or second aspects of the present invention. In other words the method of the third aspect of the invention can be used to mold a shoulder or chamfer alone onto a metallic or ceramic inner liner or it can be used to mold an outer shell having such a shoulder or chamfer around a ceramic or metallic inner liner and it may also be used for molding an outer shell formed of a bone cement material around a metallic or ceramic inner liner.

BRIEF DESCRIPTION OF THE DRAWINGS

For a better understanding of the present invention and to show how the same may be put into effect, reference will now be made, for the purposes of illustration only, to the accompanying drawings in which.

DETAILED DESCRIPTION OF THE PREFERRED EMBODIMENT(S)

The following description of the preferred embodiments concerning acetabular cups and methods of their manufacture are merely exemplary in nature and are not intended to limit the invention or its application or uses.

Figures 1, 2:
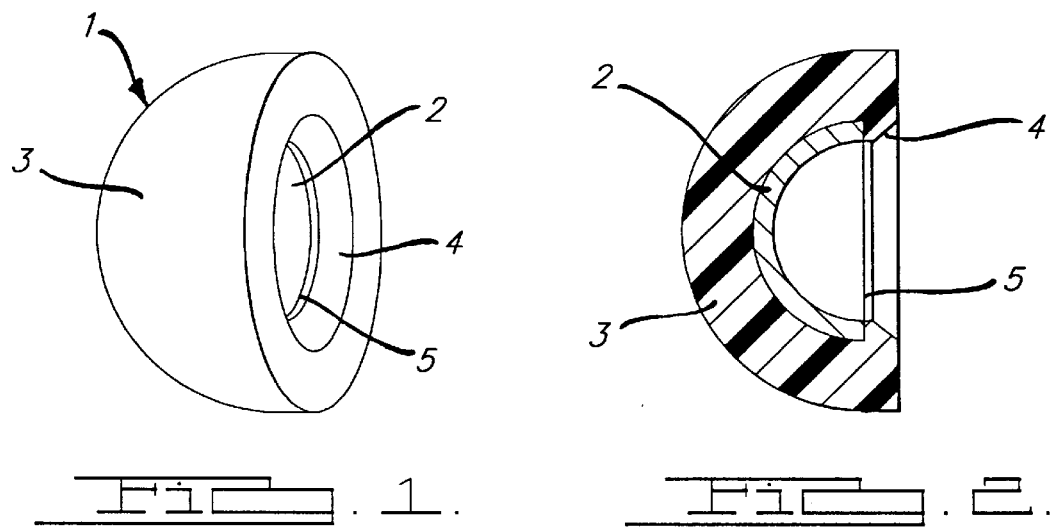
FIG. 1 is a perspective view of an acetabular cup according to the present invention.
FIG. 2 is a cross-sectional view of the acetabular cup of FIG. 1.

In FIGS. 1 and 2 there is shown an acetabular cup 1 having an inner ceramic or metallic liner 2 and an outer acetabular shell 3 of ultra high molecular weight polyethylene or polymethylmethacrylate. The outer shell 3 is provided with a tapering surface or shoulder 4 which extends around the outer edge 5 of the inner liner 2. The shoulder 4, which takes the form of a chamfer, provides a soft tapering surface acting as a limiting stop to prevent extreme ranges of motion of a femoral component received within the acetabular cup. A metallic or ceramic head or stem of a femoral component would impinge against that soft cushion 4.

Figures 3, 4:
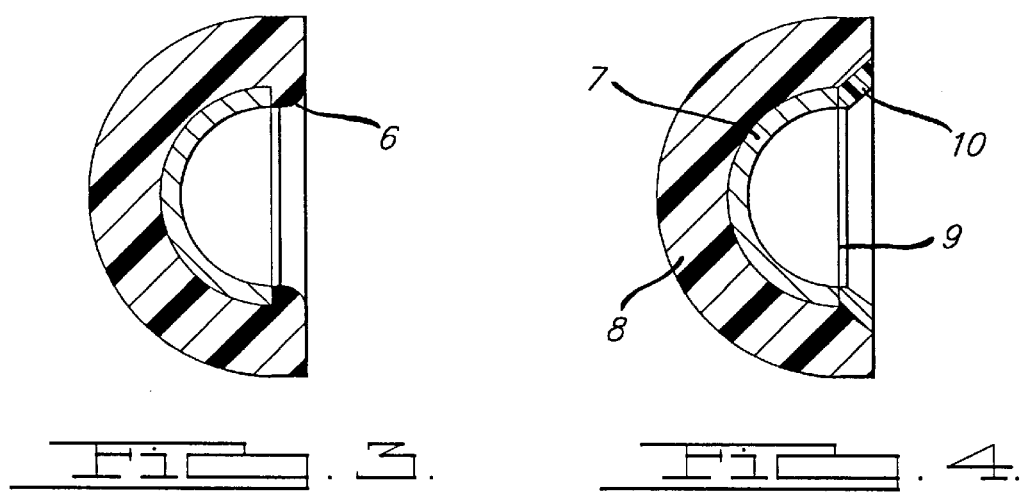
FIG. 3 is a cross-sectional view of another embodiment of the present invention.
FIG. 4 is a cross-sectional view of a further embodiment of the present invention.

The acetabular cup shown in FIG. 3 is substantially identical to that shown in FIG. 1 except that its cushion or shoulder 6 has a soft rounded contour rather than a conical tapering surface.

The acetabular cup shown in FIG. 4 has an inner ceramic or metal liner 7 and an outer acetabular shell which may be of any material, e.g. a conventional metallic acetabular shell 8. Around the outer rim 9 of the inner liner 7 there is provided an annular shoulder 10 formed of polyethylene. The polyethylene shoulder 10 may be molded on to the outer rim of the inner liner 7 or on to a suitably prepared surface of the outer acetabular shell 8.

Figure 5:
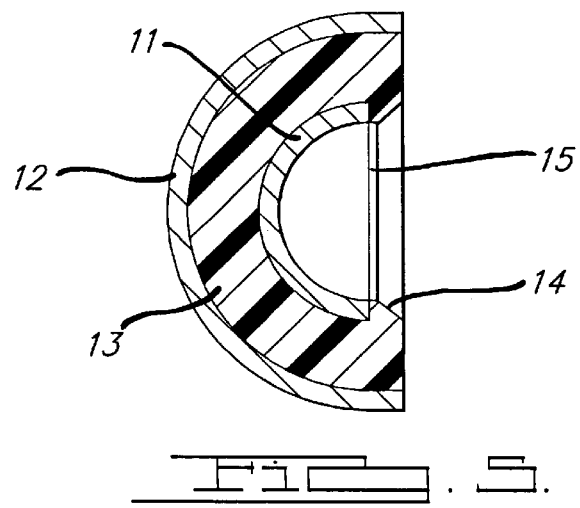
FIG. 5 is a cross-sectional view of a yet further embodiment of the present invention.

The acetabular shell shown in FIG. 5 has an inner metallic or ceramic liner 11, an outer acetabular shell 12 of any material, e.g. metal, and an intermediate component 13 into which the inner liner 11 is recessed. The intermediate component 13 is provided with a shoulder 14 which extends around the outer edge 15 of the inner liner 11 and provides a soft shoulder as with the other embodiments.

All the embodiments shown in the drawings can be manufactured by directly molding the polymeric components, eg. shoulders, intermediate components or outer shells, onto and around the inner liners.

The foregoing discussion discloses and describes merely exemplary embodiments of the present invention. One skilled in the art will readily recognize from such discussion, and from the accompanying drawings and claims, and that various changes, modifications and variations can be made therein without departing from the spirit and scope of the invention.

What is claimed is:

1. An acetabular cup for use with a head or a neck of a femoral component, said acetabular cup comprising:
   an outer shell; and
   an inner liner, said inner liner providing a bearing surface of metallic or ceramic material, wherein there is provided in a position around a rim of said inner liner a shoulder integrally formed with said outer shell, said shoulder and shell being formed of a material that is softer than that used for the head or the neck of the femoral component with which the acetabular cup is to be formed, whereby said shoulder limits the motion of the femoral component during use.

2. The acetabular cup according to claim 1, wherein said softer material from which said shell and said shoulder is manufactured is a biomedically acceptable polymeric material.

3. The acetabular cup according to claim 2, wherein said biomedically acceptable polymeric material is selected from a group consisting of polyether ether ketone (PEEK), polymethylmethacrylate (PMMA) and polyethylene (PE).

4. The acetabular cup according to claim 1 wherein said outer shell and said shoulder are manufactured from a bone cement material.

5. The acetabular cup according to claim 4, wherein said bone cement material is manufactured from an acrylic material.

6. The acetabular cup according to claim 5, wherein said acrylic material is selected from a group consisting of methylmethacrylate polymer and copolymer.

7. A method of manufacturing an acetabular cup, said method comprising the steps of:
   forming an inner liner having a bearing surface;
   forming an outer shell and a shoulder around a portion of said inner liner,
   the shoulder being integrally formed with the outer shell from a biomedically acceptable material to form a single integral unit.

8. The method according to claim 7, wherein the step of forming the outer shell and shoulder further includes the step of molding the outer shell and shoulder as a first shape and machining the first shape into its desired shape after the molding has taken place.

9. The method according to claim 7, wherein the step of forming the inner liner further includes the step of forming the inner liner from a ceramic or metallic material and wherein the step of forming the outer shell and shoulder further includes the step of forming the outer shell and shoulder as a single integral unit from a bone cement material.

10. The method according to claim 7, wherein the step of forming the inner liner further includes the step of forming the inner liner from a ceramic or metallic material and wherein the step of molding the outer shell and shoulder further includes the step of molding a polymeric outer shell and polymeric shoulder as a single integral unit around a portion of the ceramic or metallic inner liner.

11. An acetabular cup to be implanted in an acetabulum and used with a head or a neck of a femoral component, said acetabular cup comprising:
   an inner liner of metallic or ceramic material having an inner bearing surface and an outer mating surface with a rim located therebetween; and
   an outer shell having an inner mating surface and an outer connecting surface with an integrally formed shoulder positioned about said rim of said inner liner, said outer shell and shoulder being formed of a material that is softer than that used for the head or neck of the femoral component, wherein said outer mating surface of said inner liner substantially mates with said inner mating surface of said outer shell and said outer connecting surface is operable to be connected substantially adjacent the acetabulum.

12. The acetabular cup according to claim 11, wherein said inner liner is a contiguous hemispherically shaped inner liner.

* * * * *